United States Patent [19]

Finch

[11] Patent Number: 4,498,901
[45] Date of Patent: Feb. 12, 1985

[54] INTRAVENOUS MONITORING SYSTEM UTILIZING A DYNAMIC REFERENCE THRESHOLD

[75] Inventor: Dale E. Finch, McHenry, Ill.

[73] Assignee: Abbott Laboratories, North Chicago, Ill.

[21] Appl. No.: 403,383

[22] Filed: Jul. 30, 1982

[51] Int. Cl.³ ............................................. A61M 5/16
[52] U.S. Cl. ..................................... 604/65; 604/253;
128/DIG. 13; 73/861.41
[58] Field of Search ............... 128/DIG. 13, DIG. 12,
128/419, 86; 604/67, 65, 151, 153, 31, 251, 253;
315/382; 307/562; 73/861.41

[56] References Cited

U.S. PATENT DOCUMENTS

| | | | |
|---|---|---|---|
| 4,038,981 | 8/1977 | LeFevre et al. | 128/DIG. 13 |
| 4,312,355 | 1/1982 | Funke | 128/419 PG |
| 4,314,484 | 2/1982 | Bowman | 128/DIG. 13 |
| 4,383,252 | 5/1983 | Purcell et al. | 128/DIG. 13 |

*Primary Examiner*—Lee S. Cohen
*Assistant Examiner*—Steven Falk
*Attorney, Agent, or Firm*—Alan R. Thiele

[57] ABSTRACT

An intravenous monitoring system in which dynamic reference threshold circuitry is used to provide output signals indicating the presence of liquid passing through the drip chamber of an intravenous feeding apparatus. A light sensor that detects the presence of liquid passing through the drip chamber generates a detecting signal that is amplified and processed by the dynamic reference threshold circuitry. The dynamic reference threshold circuitry comprises a comparator circuit, and a D.C. component reference circuit that provides the reference threshold to the comparator circuit. The amplified detecting signal is directed both to an input of the comparator circuit and the D.C. component reference circuit. The D.C. component reference circuit uses a diode to produce a voltage drop in the amplified detecting signal and an RC circuit to both store and emit a residual signal when there is a sudden drop in the amplified detecting signal. Whenever the reference threshold exceeds the amplified detecting signal the comparator circuit generates an output signal indicating liquid passing through the drip chamber. If streaming occurs in the drip chamber an extending output signal by the comparator circuit will indicate this.

16 Claims, 5 Drawing Figures

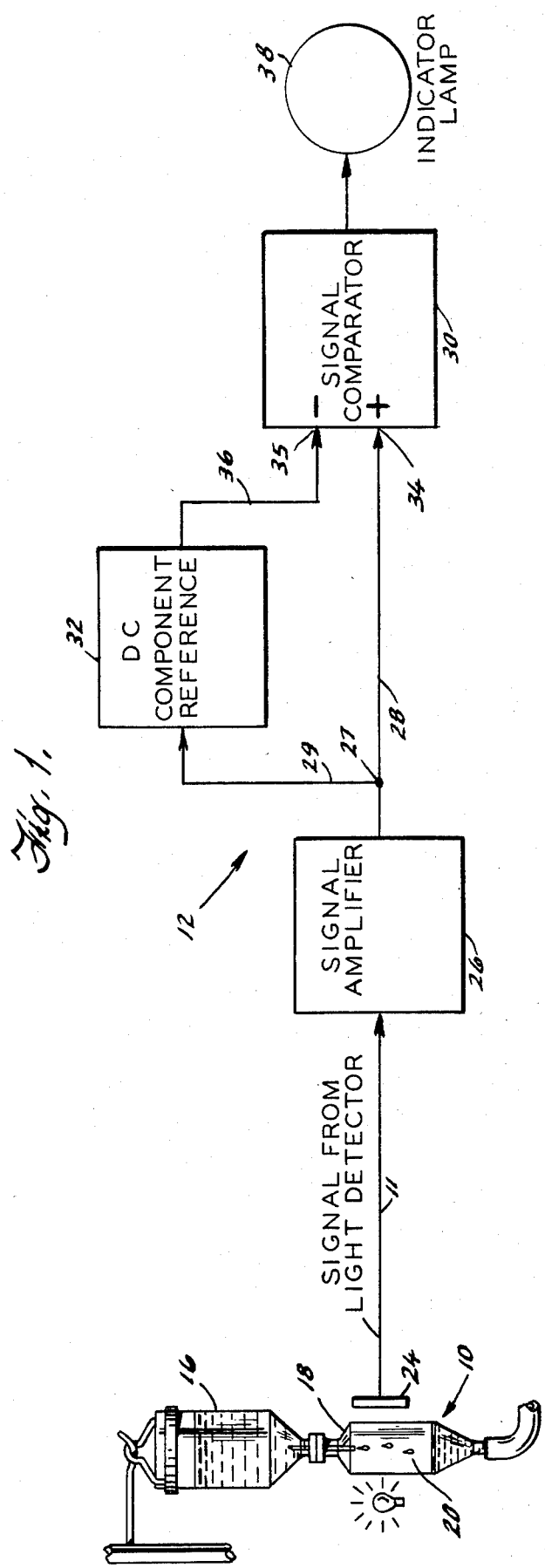
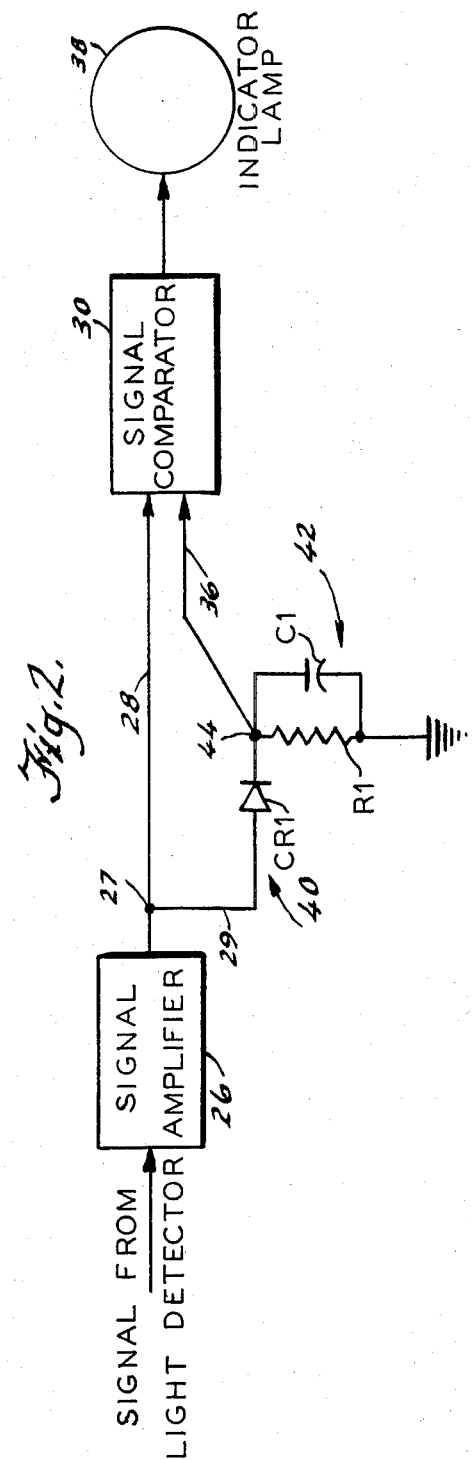

INTRAVENOUS MONITORING SYSTEM UTILIZING A DYNAMIC REFERENCE THRESHOLD

BACKGROUND OF THE INVENTION

1. Field of the Invention

The invention relates to a monitoring system for an intravenous feeding apparatus. In particular, the invention is directed to electronic circuitry which provides for the accurate detecting of the drop rate by using a dynamic reference threshold.

This application is related to a similar patent application filed with this application, by Carr et al.

2. Description of the Prior Art

It is common in medical practice to administer fluids to patients by means of an intravenous feeding apparatus. In more recent times, it has become more common to use sophisticated electro-mechanical intravenous delivery systems. As such, it has become necessary to count drops falling within the drip chamber, to both assure that the intravenous apparatus is functioning properly and also to control the drop rate or liquid flow rate.

Past intravenous monitoring systems have used drop detectors, in which a drop breaks a light beam projected onto a light sensor which in turn generates an electrical pulse which is directed to electrical processing circuitry. Campbell et al. U.S. Pat. No. 3,631,437, although not using optical detectors to detect liquid, does generate a series of electrical pulses by conductors embedded in the drip chamber which provide electrical input into logic circuitry that actuates an alarm when the drop rate frequency exceeds or falls below a specified rate.

Typical problems associated with optical detectors in intravenous monitoring systems are: the difficulty of detecting small droplets (1/60 ml. in volume) which only partially occlude the light beam; and the difficulty of detecting a steady stream of solution when the stream is generally too small (1 mm. in diameter) to obscure enough of the light beam.

A typical solution to the above-described problems is to increase the sensitivity of the signal processing circuitry. Such a solution presents its own particular problems when the walls of the drip chamber fog up by the build up of condensation. The build up of condensation results in a gradual decrease in light transmission through the drip chamber. Therefore, a typical droplet produces one signal in a clear drip chamber but a reduced signal in a fogged drip chamber. Other monitoring systems either ignore the effect of condensation or increase the gain of the system to operate in such conditions. A system that only increases gain must have a proportionally higher dynamic range.

Electronic circuitry which provides a dynamic reference threshold is sometimes used in comparator circuits to adjust the sensitivity of the threshold in response to the input. In typical circuits that provide a dynamic reference threshold, an input signal supplied by a signal generator or detector is directed to the inverting input of a comparator circuit, and the input signal is also directed to the dynamic reference threshold circuitry. The dynamic reference threshold circuitry reduces the input signal by using the voltage drop across a diode and directing this reduced input signal to the noninverting input of the comparator circuit. A capacitor is coupled to the dynamic reference circuitry between the diode and the comparator circuit so as to store a portion of the reduced input signal and to provide a residual signal when there is a sudden drop in the input signal. Therefore, when a sudden drop in the input signal occurs, the signal emitted by the dynamic reference threshold circuitry remains the same, while the input signal supplied to the comparator circuit by the signal generator or detector is reduced. The output of the comparator circuit changes when one input signal exceeds the other input signal. Examples of such circuits are illustrated by Kreda, U.S. Pat. No. 3,708,678, and Winebarger, U.S. Pat. No. 4,217,553.

SUMMARY

It is an advantage of the present invention to overcome the above-described problems associated with such intravenous monitoring systems by utilizing dynamic reference threshold circuitry. Another advantage is better control of the residual current supplied to the comparator when there is a sudden drop in the input signal, by employing an RC circuit instead of a lone capacitor.

The invention itself comprises: a signal generating means which detects the presence of liquid in the drip chamber of an intravenous feeding apparatus; and a detecting signal processing circuitry which processes the detecting signals of the signal generating means and provides an output whenever a drop is detected. In addition, the detection circuitry means provides an essentially continuous output when streaming is occurring in the drip chamber.

The particular configuration of the detecting signal processing circuitry comprises: a signal amplifier which amplifies the detecting signal from the signal generating means; a D.C. component reference circuit which comprises a dynamic reference threshold circuitry to thereby produce the dynamic reference threshold; and a signal comparator which provides an output signal whenever the input signal from the D.C. component reference threshold circuit exceeds the amplified detecting signal supplied directly from the signal amplifier. Of particular interest, is the D.C. component reference circuit, which normally supplies a reduced output voltage signal to the comparator by utilizing the generally constant voltage drop across a diode as well as its current blocking characteristic when reverse biased. Also incorporated in this circuit is an RC circuit which both stores electrical energy in its capacitor to supply a residual voltage signal whenever there is a sudden drop in the amplified detecting signal supplied by the signal amplifier and supplies the reference signal by the discharging action of the capacitor.

A sudden drop in the detecting signal corresponds to the passing of liquid through the drip chamber which at least partially occludes the light sensor of the signal generating means. The residual signal is greater than the now reduced detecting signal so that the comparator circuit produces an output signal. During intermittent drops within the drip chamber, there is a sudden drop in the detecting signal as the drop occludes the light detector. When the drop has passed, the detecting signal returns to its original state. As such, a series of intermittent output pulses are generated by the comparator indicating the drop rate. In the meantime, charge leaks out of the capacitor via the parallel resistor to provide a long term correction for the reduced detecting signal such as occurs with condensation build up. If streaming occurs in the drip chamber there is a sudden and continuous drop in the optical input signal thereby providing a longer duration output signal by the comparator than by intermittent drops. Therefore a longer output signal indicates streaming is occuring.

In another embodiment, a positive or negative voltage source is connected to the RC circuit to increase or decrease the charge in reference voltage as the condensation builds up.

BRIEF DESCRIPTION OF THE DRAWINGS

The construction and operation of the intravenous monitoring system will be more fully understood from the following detailed description taken in conjunction with the accompanying drawings:

FIG. 1 is a schematic drawing of the intravenous monitoring system;

FIG. 2 is a circuit diagram of the first embodiment of the intravenous monitoring system;

DETAILED DESCRIPTION OF THE PREFERRED EMBODIMENT

Figure 3:
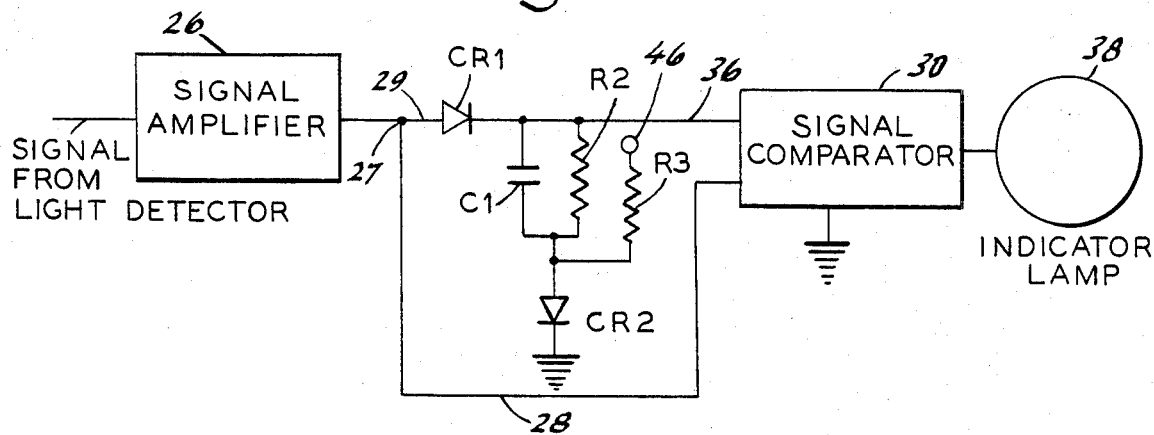
FIG. 3 is a circuit diagram of the second embodiment of the intravenous monitoring system.

FIG. 1 is a schematic representation of the subject intravenous monitoring system, wherein light sensor means 24, monitoring intravenous feeding apparatus 10, is electrically connected through conductor 11 to detecting signal processing means 12. Liquid 14 to be administered to a patient is stored within bottle 16 and flows into drip chamber 18 in the form of individual drops 20. Light from light source 22, which may be a light emitting diode, passes through drip chamber 18 and impinges upon light sensor 24, which may be a phototransistor. Whenever a liquid passes between light source 22 and light sensor 24 there occurs a sudden drop or a negative pulse in the detecting signal from light sensor 24.

The optical signal from light sensor 24 forms the detecting signal that is conducted through conductor 11 to signal amplifier 26 of detecting signal processing means 12. Signal amplifier 26 amplifies the detecting signal to a workable amplitude and directs the amplified detecting signal through output terminal 27 to conductors 28 and 29. Conductors 28 and 29 direct the amplified detecting signal to signal comparator 30 and D.C. component reference circuit 32, respectively. More specifically, conductor 28 is coupled to a first input or non-inverting input 34 of the signal comparator 30.

The D.C. component reference circuit 32 is electrically coupled through conductor 29 to signal amplifier 26, and through conductor 36 to a second input or inverting input 35 of signal comparator 30. The D.C. component reference circuit generates the dynamic reference threshold. The reference threshold comprises: a reduced output signal that mirrors the amplified detecting signal at a reduced level and is produced by the signal reduction means of the circuit; and a residual signal that is stored and emitted by the RC circuit of the D.C. component reference circuit 32 circuit. Whenever there is a sudden drop in the amplified detecting signal from signal amplifier 26 caused by liquid passing between the light source and the light detector, the amplified detecting signal drops below the reference threshold that is maintained at close to the threshold's previous level by the residual signal of the RC circuit. As in the above case, whenever the reference threshold exceeds the amplified detecting signal, the signal comparator produces an output signal that lights up indicator lamp 38.

FIG. 2 illustrates the circuity of a first embodiment of the D.C. component reference circuit. As discussed above, the amplified optical input signal is conveyed through conductor 29 from signal amplifier 26 to the D.C. component reference circuit 32 that comprises signal or voltage reduction means 40 and RC circuit 42. The voltage reduction means comprises diode CR1. RC circuit 42 is connected to ground, and comprises capacitor C1 and resistor R1 which are connected in parallel. Junction 44 of voltage reduction means 40 and RC circuit 42 is connected to conductor 36 which directs the output of these circuits to input 35 of signal comparator 30.

During the initial stages of starting up the intravenous monitoring system, current flowing through diode CR1 rapidly charges capacitor C1. After the capacitor C1 has been fully charged and the current has been stabilized; a reference threshold is established as set by the amplified detecting signal and the constant voltage drop of approximately 0.7 volts across diode CR1. As the amplified detecting signal is reduced due to condensation on the walls of the drip chamber, the reference threshold is also reduced because the charge in capacitor C1 leaks out through resistor R1 and thereby provides for a long term correction of the reduced detecting signal due to fogging.

The second embodiment illustrated in FIG. 3, is basically the same except for the addition of voltage source 46, resistor R3 and diode CR2. The specific feature of this embodiment, that is of particular interest, is voltage source 46 and resistor R2. The voltage supplied to voltage source 46 can be either positive or negative. A positive voltage source would increase the sensitivity of the comparator by reducing the voltage difference between the amplified detecting voltage from signal amplifier 26 and the reference threshold voltage supplied by D.C. component reference circuit 32. A negative voltage source would decrease the sensitivity of the comparator to change in the amplified detecting voltage by increasing the difference in the amplified detecting voltage and the reference threshold voltage.

Figure 4:
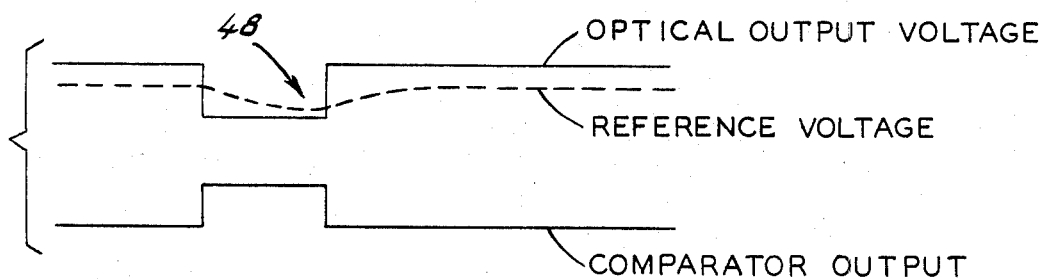
FIG. 4 is a waveform diagram of the two inputs to the comparator and the comparator output for a solitary drop event.

FIG. 4 illustrates the waveforms of the amplified detecting signal and the reference threshold that serve as inputs to the signal comparator; and the corresponding output signal generated by the signal comparator 30 in response thereto. More specifically, FIG. 4 illustrates the results of a solitary drop passing between the light source 22 and the light sensor means 24. A The solitary drop produces a negative pulse 48 in the amplified detecting voltage from signal amplifier 26 by partial obscuration of the light sensor means 24. The reference threshold voltage furnished by the D.C. component reference circuit 32 exceeds the amplified detecting voltage from signal amplifier 26 at the beginning of the pulse because of the residual signal supplied by the RC circuit. At the end of the pulse, the reference threshold voltage no longer exceeds the amplified detecting voltage from signal amplifier 26 which causes the signal comparator to not generate an output signal. When the pulse ends the reference threshold voltage moves back to its former level and the capacitor C1 of the RC circuit 42 recovers the electrical energy used in supplying the residual signal. The degrading and recovery slopes of the reference voltage are exaggerated in FIG. 4, and are not drawn to scale. As can be readily determined the signal comparator generates an output signal whenever the reference voltage exceeds the amplified detecting voltage.

Figure 5:
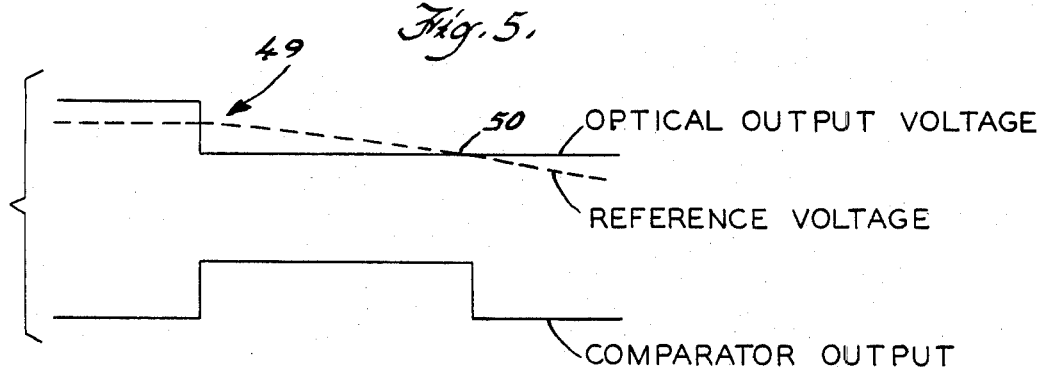
FIG. 5 is a waveform diagram of the inputs to the comparator and the comparator output for a continous stream in the drip chamber.

FIG. 5 illustrates the same waveforms discussed above in reference to FIG. 4. FIG. 5 specifically illustrates these waveforms when streaming occurs in the drip chamber 18.

When the continous stream begins there is a sudden voltage drop 49 in the amplifier detecting voltage. The reference threshold voltage exceeds the amplified detecting voltage for an extended period of time. until the RC circuit 42 has discharged below the new voltage level of the amplified detecting voltage as indicated at point 50. Correspondingly the signal comparator 30 generates an output signal for an extended period of time or from when the streaming begins until point 50 where the RC circuit is discharged below the new voltage level of the amplified detecting voltage. Therefore, by timing the output signal of the signal comparator it can be determined if streaming is occuring in the drip chamber. As before, the degrading slope of the reference voltage is exaggerated and not drawn to scale.

Indicator lamp 38 lights up whenever there is an output signal by the signal comparator 30. The indicator lamp 38 is but one example of the uses of the output signal; other uses can be activating an audible alarm or providing input to an intravenous feeding control apparatus.

The present invention can be utilized in a number of intravenous monitoring applications. So while the present invention has been disclosed in connection with the illustrated embodiments, it is not to be so limited but is to be limited solely by the claims which follow:

What is claimed is:

1. An intravenous monitoring system for an intravenous feeding apparatus having a drip chamber through which the liquid to be administered to the patient passses, comprising:

a signal voltage generating means having an output terminal and adapted to be connected to the drip chamber which generates a detecting signal voltage in response to liquid passing through said drip chamber;

a comparator means having a first input connection coupled to said output terminal of said signal voltage generating means, a second input connection and an output connection which generates an output signal voltage when a signal voltage at one of the input connections exceeds the signal voltage at the other input connection;

a D.C. component reference circuit that generates a dynamic reference threshold voltage, said D.C. component reference circuit comprises a signal voltage reduction means that is coupled between said second input connection of said comparator means and said output terminal of said signal voltage generating means, said signal voltage reduction means reduces said detecting signal voltage thus outputting a reduced output signal voltage that is less than said dynamic reference threshold voltage, and an RC circuit coupled between said signal reduction means and said second input connection of said comparator means, wherein said RC circuit stores and emits a residual signal voltage, that is also less than said dynamic reference threshold voltage, to said comparator means whenever said detecting signal voltage changes in response to liquid passing through the drip chamber, whereby when said detecting signal voltage changes in response to liquid passing through the drip chamber said dynamic reference threshold voltage exceeds said detecting signal voltage and said comparator means generates said output signal voltage in response thereto.

2. An intravenous monitoring system in accordance with claim 1 wherein said signal voltage generating means comprises a light source that passes light through said drip chamber and a light sensor that detects the light after it passes through said drip chamber and therein produces said detecting signal voltage in response to liquid passing through said drip chamber.

3. An intravenous monitoring system in accordance with claim 2 wherein said light sensor produces a negative voltage pulse when liquid passes between said light source and said light sensor.

4. An intravenous monitoring system in accordance with claim 3 wherein said signal voltage reduction means comprises a diode which produces a voltage drop in said detecting signal voltage.

5. An intravenous monitoring system in accordance with claim 4 further comprising an amplifier which is coupled between said signal voltage generating means at said output terminal of said signal voltage generating means, said amplifier aamplifies said detecting signal voltage forming an amplified detecting signal voltage.

6. An intravenous monitoring system in accordance with claim 4 further comprising an indicator lamp which is coupled to said output connection of said comparator means and which lights up in response to said output signal voltage of said comparator means.

7. An intravenous monitoring system in accordance with claim 4 further comprising a positive voltage source which is coupled to said RC circuit and provides a positive voltage thereto to increase the sensitivity of said monitoring system.

8. An intravenous monitoring system in accordance with claim 4 further comprising a negative voltage source which is coupled to said RC circuit and provides a negative voltage thereto to decrease the sensitivity of said monitoring system.

9. An intravenous monitoring system in accordance with claim 4 wherein said RC circuit is coupled to a second diode which is further connected to ground.

10. An intravenous monitoring system in accordance with claim 7 wherein said first input connection of said comparator means is a non-inverting input and said second input connection of said comparator means is an inverting input.

11. An intravenous monitoring system in accordance with claim 8 wherein said first input connection of said comparator means is a non-inverting input and said second input connection of said comparator means is an inverting input.

12. An intravenous monitoring system in accordance with claim 2 wherein said light sensor produces a positive voltage pulse when liquid passes between said light source and said light sensor.

13. An intravenous monitoring system for an intravenous feeding apparatus having a drip chamber through which the liquid to be administered to the patient passes, comprising:

an optical means adapted to be mounted in close proximity to said drip chamber which generates a detecting signal voltage in response to liquid passing through said drip chamber;

an amplifier which receives and amplifies the detecting signal voltage produced from said optical means, said amplifier having an output terminal;

a comparator means having a first input connection coupled to said output terminal of said signal voltage amplifier, a second input connection and an output connection which generates an output signal voltage when a signal voltage at one of the input connections exceeds the signal voltage at the other input connection;

a D.C. component reference circuit that generates a dynamic reference threshold voltage, said D.C. component reference circuit comprises a signal voltage reduction means that is coupled between said second input connection of said comparator means and said output terminal of said voltage amplifier, said signal voltage reduction means reduces the amplified detecting signal voltage thus outputting a reduced output signal voltage that is less than said dynamic reference threshold voltage, and an RC circuit coupled between said signal voltage reduction means and said second input connection of said comparator means, the resistor of said RC circuit forms a voltage divider with a resistor of said signal voltage reduction means thereby creating said dynamic reference threshold voltage that varies the sensitivity of the intravenous monitoring system in response to changes in said detecting signal voltage, wherein said RC circuit stores and emits a residual signal voltage, that is less than said dynamic reference threshold voltage, to said comparator means whenever said detecting signal voltage changes in response to liquid passing through the drip chamber whereby when said detecting signal voltage changes in response to liquid passing through the drip chamber said dynamic reference threshold voltage exceeds said detecting signal voltage and said comarator means generates said output signal voltage is response thereto.

14. An intravenous monitoring system for an intravenous feeding apparatus having a drip chamber through which the liquid to be administered to the patient passes, comprising:

a signal voltage generating means which is a light source and a light sensor wherein an interrupted light beam produces a negative electrical voltage from the light sensor;

a signal voltage amplifier which receives the negative electrical voltage from the light sensor and amplifies it before transmitting the amplified signal voltage to a D.C. component reference circuit, said amplifier having an output;

a D.C. component reference circuit means which separates the the signal voltage received from the amplifier into a reduced output signal voltage and a reference signal voltage, said reference circuit means comprising a parallel-connected resistor and capacitor network mounted in series with a diode; and a comparator means having a first input connection coupled to the output of said signal voltage amplifier, a second input connection connected to said D.C. component reference circuit means and an output connection through which is generated an output signal voltage when the output of the D.C. component reference circuit means exceeds the signal voltage received from said signal voltage amplifier.

15. The intravenous monitoring system of claim 14 wherein the light source is a light emitting diode.

16. The intravenous monitoring system of claim 14 wherein the light sensor is a phototransistor.

* * * * *